US010537568B2

(12) United States Patent
May

(10) Patent No.: US 10,537,568 B2
(45) Date of Patent: Jan. 21, 2020

(54) USE OF LEVOCETIRIZINE AND MONTELUKAST TO AMELIORATE INFLAMMATION FOLLOWING RADIATION EXPOSURE

(71) Applicant: Inflammatory Response Research, Inc., Santa Barbara, CA (US)

(72) Inventor: Bruce Chandler May, Santa Barbara, CA (US)

(73) Assignee: IRR, Inc., Santa Barbara, CA (US)

( * ) Notice: Subject to any disclaimer, the term of this patent is extended or adjusted under 35 U.S.C. 154(b) by 257 days.

(21) Appl. No.: 14/974,930

(22) Filed: Dec. 18, 2015

(65) Prior Publication Data

US 2016/0175301 A1 Jun. 23, 2016

Related U.S. Application Data

(63) Continuation of application No. 14/704,444, filed on May 5, 2015, now abandoned, which is a continuation of application No. 13/704,589, filed as application No. PCT/US2011/040562 on Jun. 15, 2011, now Pat. No. 9,044,479.

(60) Provisional application No. 61/355,520, filed on Jun. 16, 2010.

(51) Int. Cl.
*A61K 31/495* (2006.01)
*A61K 31/47* (2006.01)
*A61K 31/56* (2006.01)
*A61K 45/06* (2006.01)

(52) U.S. Cl.
CPC .......... *A61K 31/495* (2013.01); *A61K 31/47* (2013.01); *A61K 31/56* (2013.01); *A61K 45/06* (2013.01)

(58) Field of Classification Search
CPC ....... A61K 31/495; A61K 31/47; A61K 31/56
USPC ............................................ 514/171, 255.04
See application file for complete search history.

(56) References Cited

U.S. PATENT DOCUMENTS

| | | | |
|---|---|---|---|
| 4,801,612 A * | 1/1989 | Wei | A61K 38/2228 514/10.8 |
| 5,147,637 A | 9/1992 | Wright et al. | |
| 5,211,958 A | 5/1993 | Akkerboom et al. | |
| 5,540,225 A | 7/1996 | Schutt | |
| 6,384,038 B1 | 5/2002 | Rubin | |
| 6,790,849 B2 | 9/2004 | Rubin | |
| 7,166,640 B2 | 1/2007 | Berg | |
| 7,291,331 B1 | 11/2007 | Croft et al. | |
| 7,589,076 B2 | 9/2009 | Rieger et al. | |
| 7,791,331 B2 | 9/2010 | Servel | |
| 9,044,479 B2 | 6/2015 | May | |
| 9,522,148 B2 | 12/2016 | May | |
| 9,669,025 B2 | 6/2017 | May | |
| 9,669,026 B2 | 6/2017 | May | |
| 9,925,183 B2 | 3/2018 | May | |
| 9,937,166 B2 | 4/2018 | May | |
| 10,195,193 B2 | 2/2019 | May | |
| 10,201,537 B2 | 2/2019 | May | |
| 10,206,919 B2 | 2/2019 | May | |
| 2001/0033872 A1 | 10/2001 | Corson et al. | |
| 2002/0052312 A1 | 5/2002 | Reiss et al. | |
| 2004/0180868 A1 | 9/2004 | Mullally | |
| 2005/0256131 A1 | 11/2005 | Coester | |
| 2006/0263350 A1 | 11/2006 | Lane | |
| 2007/0020352 A1 | 1/2007 | Tripp et al. | |
| 2007/0025987 A1 | 2/2007 | Brunetta | |
| 2007/0244128 A1 | 10/2007 | Hutchinson et al. | |
| 2010/0305080 A1 | 12/2010 | O'Shea | |
| 2012/0040892 A9 | 2/2012 | Zimmer et al. | |
| 2012/0053563 A1 | 3/2012 | Du | |
| 2012/0071509 A1 | 3/2012 | Gore et al. | |
| 2012/0190691 A1 | 7/2012 | Bouyssou et al. | |
| 2012/0263764 A1 | 10/2012 | Watson | |
| 2013/0011395 A1 | 1/2013 | Spies et al. | |
| 2013/0029949 A1 | 1/2013 | Hoffmann et al. | |
| 2013/0030000 A1 | 1/2013 | Chobanian et al. | |
| 2015/0231133 A1 | 8/2015 | May | |
| 2017/0056395 A1 | 3/2017 | May | |
| 2017/0173001 A1 | 6/2017 | May | |
| 2017/0231980 A1 | 8/2017 | May | |
| 2017/0296534 A1 | 10/2017 | May | |
| 2017/0368059 A1 | 12/2017 | May | |

(Continued)

FOREIGN PATENT DOCUMENTS

| | | |
|---|---|---|
| CN | 102 895 661 | 1/2013 |
| CN | 103 505 731 | 1/2014 |
| EP | 1 769 797 | 4/2007 |

(Continued)

OTHER PUBLICATIONS

Tillement et al. Compared pharmacological characteristics in humans of racemic cetirizine and levocetirizine, two histamine H1-receptor antagonists. Biochemical Pharamcology 66 (2003) pp. 1123-1126.*
Bisgaard Hans, A Randomized Trial of Montelukast in Respiratory Syncytial Virus Postbronchiolitis, American Journal of Respiratory and Critical Care Medicine, vol. 167, No. 3, Feb. 1, 2003, pp. 379-383.
Borish, Larry, Allergic rhinitis: systemic inflammation and implications for management, The Journal of Allergy and Clinical Immunology, Dec. 1, 2003, p. 1021-1031.
Bruce May, A Proposed Model for the Treatment of Acute Inflammation, May 29, 2010, Mazatian, MX.
Bruce May, Contemporary Treatment of Influenza, Dec. 18, 2009, Santa Barbara, CA.

(Continued)

*Primary Examiner* — Jennifer M Kim
(74) *Attorney, Agent, or Firm* — Knobbe, Martens, Olson & Bear, LLP

(57) ABSTRACT

The methods and formulations include, but are not limited to, methods and formulations for delivering effective concentrations of levocetirizine and montelukast to a patient in need. The methods and formulations can comprise conventional and/or modified-release elements, providing for drug delivery to the patient. The combination can be useful during and following radiation exposure to ameliorate the inflammatory response.

8 Claims, 3 Drawing Sheets

(56) References Cited

U.S. PATENT DOCUMENTS

| | | |
|---|---|---|
| 2018/0169091 A1 | 6/2018 | May |
| 2018/0185357 A1 | 7/2018 | May |

FOREIGN PATENT DOCUMENTS

| | | |
|---|---|---|
| EP | 2520292 A1 | 7/2012 |
| JP | 2001-511134 | 8/2001 |
| JP | 2001-526232 | 12/2001 |
| JP | 2002-511425 | 4/2002 |
| JP | 2004-536097 | 12/2004 |
| JP | 2009-520711 | 5/2009 |
| JP | 2009-525952 | 7/2009 |
| JP | 2011-500847 | 1/2011 |
| JP | 2012-519207 | 8/2012 |
| KR | 10-2001-0033485 | 4/2001 |
| RU | 2442789 | 6/2010 |
| WO | WO 1995/09652 A1 | 4/1995 |
| WO | WO 99/32125 A1 | 7/1999 |
| WO | WO 99/52553 A1 | 10/1999 |
| WO | WO 03/002098 | 1/2003 |
| WO | WO 2003/002109 A2 | 1/2003 |
| WO | WO 2008/100539 A1 | 8/2008 |
| WO | WO 2009/022327 | 8/2008 |
| WO | WO 2008/106429 | 9/2008 |
| WO | WO 2009/055729 | 4/2009 |
| WO | WO 2010/107404 A1 | 9/2010 |
| WO | WO 2011/041462 A2 | 4/2011 |
| WO | WO 2011/094209 | 8/2011 |
| WO | WO 2011/159821 A1 | 12/2011 |
| WO | WO 2012/064301 A2 | 5/2012 |
| WO | WO 2012/092594 | 7/2012 |
| WO | WO 2013/012199 A1 | 1/2013 |
| WO | WO 2014/090990 | 6/2014 |
| WO | WO 2017/210417 | 12/2017 |

OTHER PUBLICATIONS

Ciebiada M, et al. Montelukast with desloratadine or levocetirizine; Annals of Allergy, Asthma & Immunology, Nov. 2006; 8 pages.

Hong et al., Uticaria and Angioedema, Cleveland Clinic Center for Continuation Education, Aug. 2010, pp. 1-15.

International Search Report and Written Opinion dated Nov. 3, 2011, issued in connection with PCT/US2011/040562.

Khoury, Paneez et al., Effect of montelukast on bacterial sinusitis in allergic mice, Annals of Allergy, Asthma & Immunology, Arlington Heights, IL, US, vol. 97, No. 3, Sep. 1, 2006, pp. 329-335.

Kurowski, M., et al., Montelukast plus cetirizine in the prophylactic treatment of seasonal allergic rhinitis: influence of clinical symptoms and nasal allergic inflammation, Allergy, 2004, pp. 280-288, vol. 59, United Kingdom.

Min Jin-Young et al., Levocetirizine inhibits rhinovirus-induced bacterial adhesion to nasal epithelial cells through down-regulation of cell adhesion molecules, Annals of Allergy, Asthma & Immunology, Arlington Heights, IL, US, vol. 108, No. 1 Sep. 22, 2011.

Moiz; Formulation and evaluation; Jan. 2011; 22 pages.

Parker et al., 48 Year Old Man With Recurrent Sinusitis, Jan. 2001; 2 pages.

Peroni et al., Combined cetirizine-montelukast preventative treatment for food-dependent exercise-induced anaphylaxis, Annals of Allergy, Asthma, & Immunology, Mar. 1, 2010, vol. 104, pp. 272-273.

Schad, C. et al., Effect of Montelukast on Pro-inflammatory Cytokine Production During Naturally Acquired Viral Upper Respiratory Infections (vURIs) in Adults, Journal of Allergy and Clinical Immunology, Elsevier, Amsterdam, NL, vol. 121, No. 2. Feb. 1, 2008, p. S74.

Tang, Angela, A practical guide to anaphylaxis, American Family Physician, Oct. 1, 2003, vol. 68, No. 7, pp. 1325-1333.

Tillie-Leblond et al., Relation between inflammation and symptoms in asthma, Allergy, vol. 64, No. 3, Mar. 1, 2009, p. 354-367.

International Preliminary Report on Patentability received in PCT Application No. PCT/US2011/040562, dated Jan. 3, 2013 in 6 pages.

Tillement et al., "Compared Pharmacological Characteristics in Humans of Racemic Cetirizine and Levocetirizine, Two Histamine $H_1$-Receptor Antagonists", Biochemical Pharmacology, 2003, pp. 1123-1126.

Centers for Disease Control and Prevention, Acute Radiation Syndrome: A Fact Sheet for Clinicians, http://emergency.cdc.gov/radiation/arsphysicianfactsheet.asp, Page Last updated: Dec. 10, 2015.

Weiss, J., et al. History and Development of Radiation-Protective Agents 85 Int. J. Radiat. Biol. 539-573 (2009).

Williams, J., et. al. Animal Models for Medical Countermeasures to Radiation Exposure 173 Radiation Research 557-578, (2010).

Al-Ahmad, Mona, "Omalizumab Therapy in Three Patients with Chronic Autoimmune Urticaria", Annals of Saudi Medicine, vol. 30, No. 6, Nov.-Dec. 2010, pp. 478-481.

Clinical Surgery, 1999, Oct. 3, vol. 54, No. 11, Special Issue, pp. 13-15.

Namazi, M.R. "Cetirizine and Allopurinol as Novel Weapons Against Cellular Autoimmune Disorders", International Immunopharmacology, 2004, vol. 4, pp. 349-353.

Singh-Franco et al., "Levocetirizine for the Treatment of Allergic Rhinitis and Chronic Idiopathic Urticaria in Adults and Children", Clinical Therapeutics, vol. 31, No. 8, Aug. 2009, pp. 1664-1687.

Dávila et al., "Effect of $H_1$ Antihistamines Upon the Cardiovascular System", Journal of Investigational Allergology and Clinical Immunology, 2006, vol. 16, No. 1, pp. 13-23.

Eccles, Ron, "Understanding the Symptoms of the Common Cold and Influenza", The Lancet Infectious Diseases, R(1) Nov. 2005, vol. 5, No. 11, pp. 718-725.

El-Shanawany et al., "Clinical Immunology Review Series: An Approach to the Patient with Anaphylaxis", British Society for Immunology, Clinical and Experimental Immunology, 2008, vol. 153, pp. 1-9.

Fedson, David, "A Practical Treatment for Patients with Ebola Virus Disease", Journal of Infectious Diseases, Aug. 25, 2014, pp. 5.

Fedson, David, "Treating Influenza with Statins and Other Immunomodulatory Agents", Antiviral Research, Sep. 2013, vol. 99, No. 3, pp. 417-435.

Heneka et al., "Innate Immune Activation in Neurodegenerative Disease", Nature Reviews, Immunology, Jul. 2014, vol. 14, pp. 463-477.

Jang et al., "Levoceterizine Inhibits Rhinovirus-Induced ICAM-1 and Cytokine Expression and Viral Replication in Airway Epithelial Cells", Antiviral Research, Mar. 2009, vol. 81, No. 3, pp. 226-233.

Jensen et al., "Sensing of RNA Viruses: a Review of Innate Immune Receptors Involved in Recognizing RNA Virus Invasion", Journal of Virology, Mar. 2012, vol. 86, No. 6, pp. 2900-2910.

Jianxin et al., "Therapeutic Effectiveness Analysis of Montelukast in Therapy of Anaphylactic Purpura", Journal of Clinical and Experimental Medicine, May 2010, vol. 9, No. 10, pp. 782-783.

Kuna et al., "Two Phase II Randomized Trials on the CR Th2 Antagonist AZD1981 in Adults with Asthma", Drug Design, Development and Therapy, 2016, vol. 10, pp. 2759-2770.

Luthra et al., "Mutual Antagonism between the Ebola Virus VP35 Protein and the RIG-1 Activator PACT Determines Infection Outcome", Cell Host Microbe, Jul. 17, 2013, vol. 14, No. 1, pp. 1-23.

Mathiesen et al., "On the Mechanism of Interaction of Potent Surmountable and Insurmountable Antagonists with the Prostaglandin D2 Receptor CRTH2", Molecular Pharmacology, 2006, vol. 69, No. 4, pp. 1441-1453.

McElroy et al., Ebola Hemorrhagic Fever: Novel Biomarker Correlates of Clinical Outcome, Journal of Infectious Disease, Aug. 15, 2014, vol. 210, No. 4, pp. 558-566.

Modrykamien, MD et al., "The Acute Respiratory Distress Syndrome", Proceedings (Baylor University Medical Center) 2015, vol. 28, No. 2, pp. 163-171.

Nonaka et al., "Prolonged Activation of NF-κB Following Traumatic Brain Injury in Rats", Journal of Neurotrauma, Nov. 1999, vol. 16, No. 11, pp. 1023-1034.

(56) References Cited

OTHER PUBLICATIONS

Popov et al., "A Comparison of Levocetirizine and Desloratadine in the Histamine-Induced Wheal and Flare Response in Human Skin in Vivo", Inflammatory Research, Jun. 2006, vol. 55, No. 6, pp. 241-244.
"Prostaglandin DP2 receptor", Wikipedia, https://en.wikipedia.org/wiki/Prostaglandin_DP2_receptor, Aug. 25, 2017, pp. 9.
Pushparaj et al., "The Cytokine Interleukin-33 Mediates Anaphylactic Shock", with Retraction and Correction, Proceeding of the National Academy of Sciences of the United States of America (PNAS), Jun. 16, 2009, vol. 106, No. 24, pp. 9773-9778.
Roumestan et al., "Histamine H1-receptor antagonists inhibit nuclear factor-kappaB and activator protein-1 activities via H1-receptor-dependent and -independent mechanisms", Clinical and Experimental Allergy, Jun. 2008, vol. 38, No. 6, pp. 947-956.
Spiropoulou et al., "RIG-I Activation Inhibits *ebolavirus* Replication", Virology, 2009, 392, pp. 11-15.
Taber's® Cyclopedic Medical Dictionary, "Trauma", 18th Edition, 1997, pp. 1988-1989.
Wong et al., "Characterization of Host Immune Responses in Ebola Virus Infections", Expert Review of Clinical Immunology, 2014, vol. 10, No. 6, pp. 781-790.
Zana, Larry, "Qrono—Reformulating known, approved drugs", as printed Jun. 23, 2014, pp. 12.
Zhang et al., "Contrastive Observation of Loratadine and Cetirizine in Therapy of Anaphylactic Purpura", Chinese Remedies & Clinics, May 2008, pp. 65-66.
Deb et al., "Pathophysiologic Mechanisms of Acute Ischemic Stroke: An Overview with Emphasis on Therapeutic Significance Beyond Thrombolysis", Pathophysiology, 2010, vol. 17, pp. 197-218.
Elting et al., "Comparison of Serum S-100 Protein Levels Following Stroke and Traumatic Brain Injury", Journal of the Neurological Sciences, 2000, vol. 181, pp. 104-110.
Kronenberg et al., "Symptomatic Treatment of Uncomplicated Lower Urinary Tract Infections in the Ambulatory Setting: Randomised, Double Blind Trial", BMJ, 2017, vol. 359, No. J4787, pp. 10.
McKinney et al., "The Immunopatholgy of ANCA-Associated Vasculitis", Semin Immunopathol, 2014, vol. 36, pp. 461-478.
Pellicane, MD, et al., "Calorie and Protein Intake in Acute Rehabilitation Inpatients with Traumatic Spinal Cord Injury Versus Other Diagnoses", Topics in Spinal Cord Injury Rehabilitation, 2013, vol. 19, No. 3, pp. 229-235.
Quercia et al., "Adalimumab Desensitization after Anaphylactic Reaction", Allergy, 2010, vol. 65, No. 92, pp. 242-243.
Radlińska et al., "Montelukast—Recent Advances in Determining the Role of Leukotriene Inhibitor in Allergic Diseases", International Review of Allergology and Clinical Immunology, Jan. 2011, vol. 17:1-2, pp. 35-39.
Vasculitis Foundation, http://vasculitisfoundation.org/education/forms/urticarial-vasculitis/, 2017.
Zappalà et al., "Traumatic brain injury and the frontal lobes: What can we gain with diffusion tensor imaging?" Cortex, 2011, pp. 1-10.
Murdoch et al., "Chronic Inflammation and Asthma," Mutation Research, vol. 690, (2010), pp. 24-39.
Medzhitov, "Origin and Physiological Roles of Inflammation," R. Nature, vol. 454, Jul. 24, 2008, pp. 428-435.
Rosen et al., "New Approaches to Radiation Protection," Frontiers in Oncology, vol. 4 (381), Jan. 2015, pp. 1-15.
Bernier et al., "Consensus guidelines for the management of radiation dermatitis and coexisting acne-like rash in patients receiving radiotherapy plus EGFR inhibitors for the treatment of squamous cell carcinoma of the head and neck," Annals of Oncology, vol. 19 (1), Jan. 2008, pp. 142-149.

* cited by examiner

USE OF LEVOCETIRIZINE AND MONTELUKAST TO AMELIORATE INFLAMMATION FOLLOWING RADIATION EXPOSURE

RELATED APPLICATIONS

This patent application is a continuation of U.S. patent application Ser. No. 14/704,444, filed May 5, 2015, which is a continuation of U.S. patent application Ser. No. 13/704,589, filed Dec. 14, 2012, which is the U.S. National Phase entry of International Application PCT/US2011/040562, filed Jun. 15, 2011, which claims priority from U.S. Provisional Patent Application Ser. No. 61/355,520, filed Jun. 16, 2010, all of which are incorporated by reference herein in their entirety, including any drawings.

BACKGROUND

Influenza may include an acute contagious viral infection characterized by acute inflammation of the respiratory tract and by fever, chills, muscular pain, and prostration. Influenza may also include any of various viral infections of domestic animals characterized generally by acute inflammation, fever and respiratory involvement. Although not as severe as flu, a common cold, which can be caused by more than 200 different viruses, may include congestion of the head and chest.

Typical attempts to fight influenza use vaccines. Unfortunately this does not attack the viruses at their primary entrance and exit from the human body, the nose and throat. Further, new vaccines are needed for new strains of the virus and are not easily scalable. Each year, vaccines are only created for a handful of flu strains, leaving people without comprehensive influenza protection; there would be an estimated six month delay to create a vaccine in response to a pandemic. Moreover, vaccines cannot be used for people who have an allergy to chicken eggs or thimerosal, people who have had a severe reaction to an influenza vaccination, people who developed Guillain-Barre syndrome (GBS) within 6 weeks of getting an influenza vaccine, children less than 6 months of age, and people who have a moderate-to-severe illness with a fever.

Other attempts to fight influenza have used M2 channel blockers and neuraminidase inhibitors (e.g. Tamiflu® and Relenza®). Unfortunately, the existing treatment of influenza, e.g., the prototype neuraminidase inhibitor, oseltamivir (Tamiflu®), has not been shown to decrease the incidence of lower respiratory tract infections in patients with influenza. Moreover, zanamivir (Relenza®) is not indicated in patients with underlying respiratory or heart disease or below the age of 7. "In conclusion, neuraminidase inhibitors have modest effectiveness against the symptoms of influenza in otherwise healthy adults. Neuraminidase inhibitors might be regarded as optional for reducing symptoms of seasonal influenza." Cochrane review article: Jefferson T, et. al. Neuraminidase inhibitors for preventing and treating influenza in healthy adults. BMJ 8 Dec. 2009; 339:b5106.

There remains an important unmet need for a therapeutic approach for treating influenza, common cold, acute inflammation, subacute inflammation, and chronic inflammation which addresses one or more of the underlying pathologic mechanisms.

SUMMARY

One embodiment is directed to methods, formulations and kits for treating influenza, common cold and acute, subacute, and chronic inflammation. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

In some embodiments, the methods of treatment, formulations and kits may include e.g., a bilayer tablet, comprising levocetirizine and montelukast in separate layers, for daily administration. Alternatively, each medication may be administered separately (one tablet of levocetirizine and one tablet of montelukast per day in the evening). In some embodiments, a combination of levocetirizine and montelukast, either as a single formulation or as separate formulations, may be administered for 1, 2, 3, 4, 5, 6, 7, 8, 9, 10, 11, 12, 13, 14, or 15 days for the treatment of viral infections. In several embodiments, the viral infection may be an Upper Respiratory Tract Infection (URI), for example the common cold or influenza. The bilayer tablets or the separate tablets may be packaged in a blister pack supplied for a 7 to 10 day course of therapy, with instructions including indications, administration instructions and precautions. In some embodiments, a combination of levocetirizine and montelukast, either as a single formulation, such as a bilayer tablet, or as separate formulations, may be administered for approximately 15, 20, 30, 60, 90, 120, 150, 180, 210, 240, 270, 300, 330, 360 days or more for the treatment of chronic inflammation. The bilayer tablets or the separate tablets may be packaged in a blister pack supplied for a 30 day course of therapy, with instructions including indications, administration instructions and precautions.

In some embodiments, a method of treating influenza comprises administering to an individual a first compound and a second compound, where the first compound is an antihistamine and the second compound is a leukotriene receptor antagonist.

In some embodiments, a method of treating influenza comprises administering to an individual a first compound and a second compound, where the first compound is levocetirizine and the second compound is montelukast.

In some embodiments the first compound and the second compound are administered more or less simultaneously. In other embodiments the first compound is administered prior to the second compound. In yet other embodiments, the first compound is administered subsequent to the second compound.

In another aspect, the present embodiments relate to a method of reducing influenza symptoms in an individual comprising identifying an individual in need thereof and treating that individual to antagonize leukotriene receptor activity and to block histamine receptors.

In another aspect, the present embodiments relate to a method of reducing the duration of influenza symptoms in an individual comprising identifying an individual in need thereof and treating that individual to antagonize leukotriene receptor activity and to block histamine receptors.

In some embodiments, a method of treating a common cold comprises administering to an individual a first compound and a second compound, where the first compound is an antihistamine and the second compound is a leukotriene receptor antagonist.

In some embodiments, a method of treating a common cold comprises administering to an individual a first compound and a second compound, where the first compound is levocetirizine and the second compound is montelukast.

In some embodiments the first compound and the second compound are administered more or less simultaneously. In other embodiments the first compound is administered prior to the second compound. In yet other embodiments, the first compound is administered subsequent to the second compound.

In another aspect, the present embodiments relate to a method of reducing symptoms of a common cold in an individual comprising identifying an individual in need thereof and treating that individual to antagonize leukotriene receptor activity and to block histamine receptors.

In another aspect, the present embodiments relate to a method of reducing the duration of symptoms of a common cold in an individual comprising identifying an individual in need thereof and treating that individual to antagonize leukotriene receptor activity and to block histamine receptors.

Some embodiments relate to a method of treating IgE-mediated inflammation.

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating non-IgE-mediated inflammation.

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating combined non-IgE-mediated and IgE-mediated inflammation.

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating chronic rhinosinusitis.

In some embodiments, the treating step of the above method comprises administering to the individual a first compound and a second compound, where the first compound is an antihistamine and the second compound is a leukotriene receptor antagonist.

In some embodiments, the treating step of the above method comprises administering to an individual a first compound and a second compound, wherein the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

In yet another aspect, the present embodiments relate to a method of reducing the size and or number of polyps and/or mucosal disease or inflammation in an individual with chronic rhinosinusitis comprising identifying an individual in need thereof and treating that individual to block histamine receptors and to antagonize leukotriene receptor activity.

In yet another aspect, the present embodiments relate to a method of reducing the size and or number of polyps and/or mucosal disease or inflammation in an individual with chronic rhinosinusitis comprising identifying an individual in need thereof and treating that individual with levocetirizine and montelukast.

Several embodiments relate to a method of treating acute bacterial rhinosinusitis (ABRS).

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating chronic rhinosinusitis without nasal polyposis (CRSsNP).

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating chronic rhinosinusitis with nasal polyposis (CRSwNP).

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating allergic fungal rhinosinusitis (AFRS).

In some embodiments, the treating step of the above method comprises administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

Several embodiments relate to a method of treating a bacterial infection in an individual comprising administering to the individual a first compound and a second compound, where the first compound is an antihistamine and the second compound is leukotriene receptor antagonist.

In some embodiments, the treating step of the above method comprises administering to an individual a first compound and a second compound, where the first compound is levocetirizine and the second compound is montelukast.

In some embodiments the first compound and the second compound are administered nearly simultaneously. In other embodiments the first compound is administered prior to the second compound. In yet other embodiments, the first compound is administered subsequent to the second compound.

BRIEF DESCRIPTION OF THE DRAWINGS

FIG. 2A and FIG. 2B show CT images taken prior to treatment. FIG. 2C and FIG. 2D show CT images taken after three and one-half weeks of therapy with the combined medication, levocetirizine plus montelukast.

FIG. 3A shows an endoscopic photograph taken at time zero, left intranasal (at 6-10 o'clock) and left maxillary (at three o'clock) polyps with chronically inflamed hyperplastic mucosa are shown. FIG. 3B shows an endoscopic photograph taken at four months post-initiation of combined levocetirizine plus montelukast therapy. FIG. 3C shows an endoscopic photograph taken at 10 months post-initiation of combined levocetirizine plus montelukast therapy.

DETAILED DESCRIPTION

Figure 1:
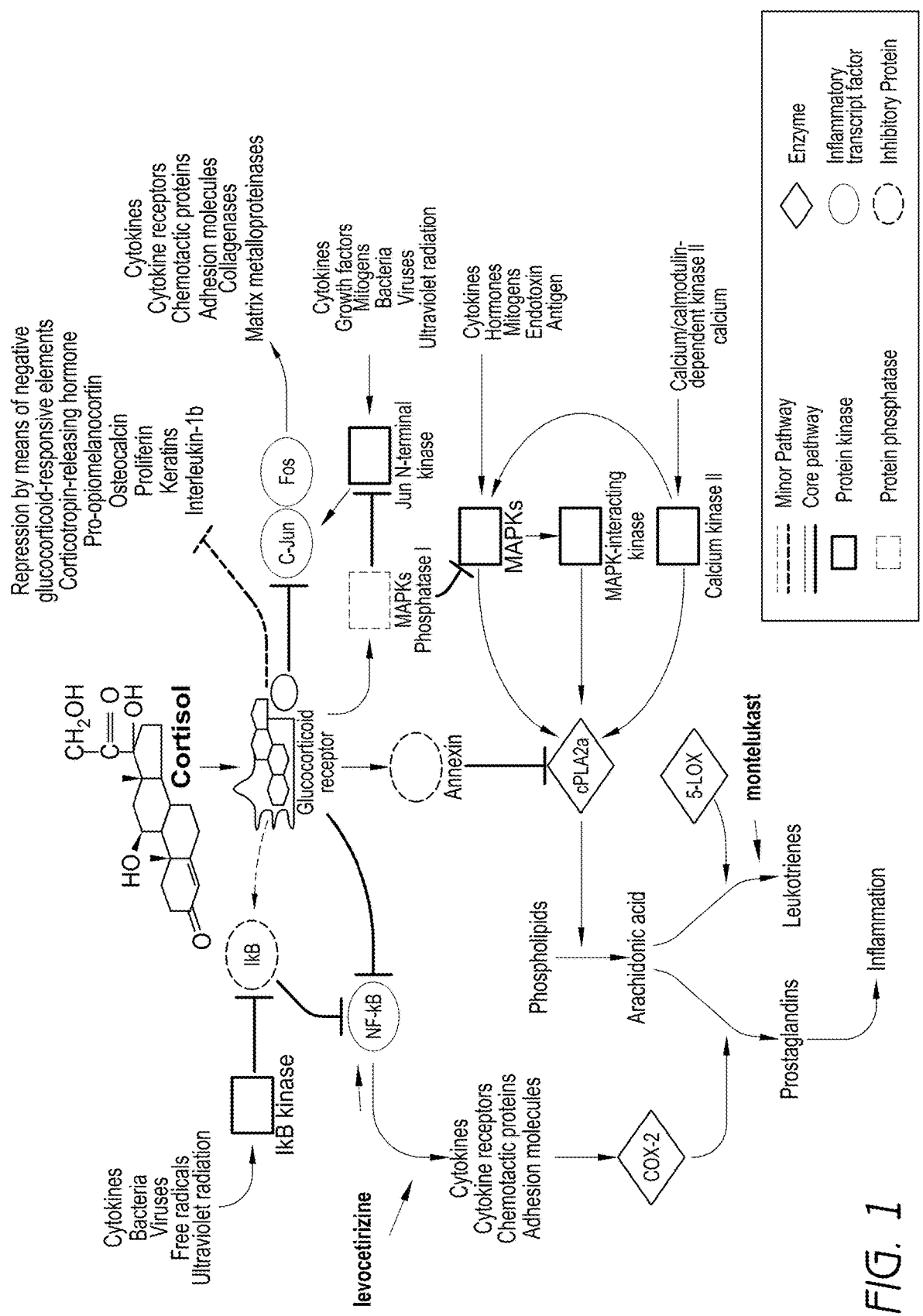
FIG. 1 shows a diagram of the proposed anti-inflammatory mechanism of action of levocetirizine and montelukast utilizing a steroid model pathway.

The present embodiments relate to the combination of levocetirizine and montelukast as a medicament for the treatment of acute, subacute and chronic inflammation. Several embodiments relate to the combination of levocetirizine and montelukast for the treatment of non-IgE-mediated, IgE-mediated, and/or combined non-IgE-mediated and IgE-mediated inflammation. Traditional allergic rhinitis is an IgE mediated disease; up to 70-80% of patients with asthma also have allergic rhinitis (atopic asthma). Administration of levocetirizine and montelukast in combination exhibits synergistic effects and unexpectedly superior results in the treatment of influenza, common cold, allergic rhinitis and acute, subacute, and chronic inflammation. Moreover, combinations of levocetirizine and montelukast can be used safely in conjunction with many existing treatment protocols.

Levocetirizine is an antihistamine and montelukast is a leukotriene receptor antagonist. As described herein, synergy between levocetirizine and montelukast shortens the course of the disease processes, thereby decreasing morbidity and mortality. This combined therapy also can improve quality of life from the amelioration of symptoms/side effects/disease process itself, and can decrease health-care costs. This syngergistic effect can be observed in the use of a combination of levocetirizine and montelukast to treat non-IgE-mediated inflammation and combined non-IgE-mediated and IgE-mediated inflammation. Not wishing to be bound by a particular theory, the non-IgE-mediated response may be related, at least in part, to the fact that both levocetirizine and montelukast affect eosinophil migration, the leukocyte that is considered a hallmark of inflammation.

Levocetirizine, a potent H1-antihistamine, acts primarily by down-regulating the H1 receptor on the surface of mast cells and basophils to block the IgE-mediated release of histamine which cause the cardinal symptoms of allergic rhinitis: sneezing, rhinorrhea, nasal congestion, itchy palate and itchy red and watery eyes. Levocetirizine offers a short time to peak plasma level, 0.9 hr., a short time to steady state level, 40 hours, a low volume of distribution, 0.4 L/kg, and an enhanced receptor affinity of 5× over first generation mepyramine in an acidic pH (many acute inflammatory disease states are associated with acidosis, a low physiologic pH). Levocetirizine has a 24 hour receptor occupancy of ~75%, the highest of the commercially available antihistamines. Receptor occupancy of the second generation antihistamines appears to correlate with the pharmacodynamic activity in skin wheal and flare studies and with efficacy in allergen challenge chamber studies. Levocetirizine is approved in the US for the treatment of perennial allergic rhinitis and chronic idiopathic urticaria down to six months of age.

Levocetirizine has been objectively established as the most potent of the five modern generation antihistamines through histamine induced wheal and flare data. For example, levocetirizine at 5 mg per day is more effective than fexofenadine at its commonly prescribed dose of 180 mg per day in the United States. In Europe the adult dose is 120 mg per day. Levocetirizine has a lower volume of distribution, greater histamine receptor affinity in an inflamed state (low pH), and greater receptor occupancy at 24 hours at physiologic doses than fexofenadine. The corresponding values are shown in Table I.

TABLE I

COMPARISON BETWEEN FEXOFENADINE AND LEVOCETIRIZINE

|  | Fexofenadine | Levocetirizine |
| --- | --- | --- |
| Vd-L/kg | 5.6 L/kg | 0.4 L/kg |
| Receptor affinity in an acidic ph | increased 2× | increased 5× |
| Histamine receptor occupancy at 24 hours | ~25% | ~75% |
| Steady-state level | 3 days | 40 hours |

Levocetirizine decreases human rhinovirus titers in vitro by log-2. Not to be bound by a particular theory, the cellular mechanism of action is a proposed reduction of the activation of the intracellular protein complex NF-kB (nuclear factor kappa B) which is in turn responsible for the reduction of I-CAM-1. I-CAM-1, a transmembrane protein, is viewed as the portal of entry of human rhinovirus into the cell. Rhinovirus can be found in ~50% of cases of acute asthma and is responsible for 30-50% cases of the 'common cold.' A one-log reduction in viral titers has been independently determined to correlate with improved symptoms. In addition, levocetirizine has been shown to decrease eosinophil migration and decrease inflammatory mediators, IL-4, IL-6, and IL-8. IL-6, a signaling protein, regulates in part: fever, the body's response to trauma, and the acute (immediate) phase of the allergic reaction.

Montelukast, a leukotriene receptor antagonist, acts by binding with high affinity and selectivity to the CysLT1 receptor to inhibit the physiologic actions of the leukotriene LTD4. Leukotrienes are fatty signaling molecules whose effects include airway edema, smooth muscle contraction and altered cellular activity associated with the inflammatory process. Overproduction of leukotriene is a major cause of inflammation in asthma and allergic rhinitis. The cysteinyl leukotrienes (LTC4, LTD4, LDE4) are products of arachidonic acid metabolism. These leukotrienes are released from various cells including mast cells and eosinophils. They bind to receptors in the human airway and on other pro-inflammatory cells including eosinophils and certain myeloid stem cells. The cysteinyl leukotrienes have been correlated with the pathophysiology of asthma and allergic rhinitis.

Leukotriene $D_4$ is the most potent of the cysteinyl leukotrienes in contracting airway smooth muscle. Leukotriene receptors, such as $CysLT_1$, are found throughout the cells of the respiratory tree (including airway smooth muscle cells and airway macrophages) as well as on other pro-inflammatory cells in the body, particularly eosinophils and certain myeloid stem cells. Leukotrienes also function to promote the recruitment of eosinophils, dendritic cells and T cells. Eosinophil infiltration is considered by some authorities as a hallmark of inflammation.

Montelukast is FDA approved in the US for the treatment of perennial allergic rhinitis, asthma, seasonal allergic rhinitis, and exercised induced bronchospasm. Montelukast has been shown to be ineffective in improving asthma control or cold symptom scores caused by experimental rhinovirus infection. See Kloepfer K M, et al., Effects of montelukast in patients with asthma after experimental inoculation with human rhinovirus 16. Annals Allergy Asthma Immunology. 2011; 106:252-257. Unlike levocetirizine, no decrease in viral shedding was observed in rhinovirus-infected individuals treated with montelukast and there was no significant difference in reported cold symptom scores compared to placebo-treated individuals. Analysis of secondary outcomes suggests that montelukast may protect against reductions in lung function and increases in sputum eosinophils caused by common cold infections. During the recovery phase the percentage of sputum eosinophils was elevated in the placebo group, while the montelukast group remained at baseline levels. Further, peak expiratory flow was not decreased in the montelukast-treated patients. Other studies have shown that montelukast treatment has no effect on the respiratory symptoms of patients with acute respiratory syncitial virus bronchiolitis. See Bisgaard, H., et al., Study of montelukast for the treatment of respiratory symptoms of post-respiratory syncitial virus bronchiolitis in children, Am. J. Respir. Crit. Care Med., 2008; 178:854-860; and Proesmans, M., et al., Montelukast does not prevent reactive airway disease in young children hospitalized for RSV bronchiolitis, Acta Paediatr. 2009; 98:1830-34. However, some studies indicate that treatment with montelukast reduced the number of days with worsened asthma symptoms and unscheduled doctor's visits in children with mild allergic asthma and resulted in a modest reduction of symptoms in children with recurrent wheezing when given at the first sign of upper respiratory tract illness. See Sears, M. R. and Johnston, N. W., Understanding the September asthma epidemic. J. Allergy Clin. Immunol. 2007; 120:526-29; Bacharier, L. B., et al., Episodic use of an inhaled corticosteroid or leukotriene receptor antagonist in preschool children with moderate-to-severe intermittent wheezing. J. Allergy Clin. Immunol. 2008; 122:1127-35.

Montelukast reaches a steady state level, like the second generation antihistamine, levocetirizine, in less than two days. Unlike other currently available leukotriene modulators, zileuton and zafirlukast, routine monitoring of liver function tests is not required. There are no drug interactions with warfarin, theophylline, digoxin, terfenadine, oral contraceptives, or prednisone.

The two molecules are safe, i.e., FDA approved in the United States for allergic disorders down to age six months. They can be given primarily or in conjunction with many of the existing therapeutic protocols for the treatment of inflammation, including but not limited to, influenza, acute asthma and the common cold. Both medications are pregnancy category B (Table II).

TABLE II

PREGNANCY CATEGORY DEFINITIONS

| Category | Definition | Explanation |
| --- | --- | --- |
| A | Generally acceptable | Controlled studies in pregnant women show no evidence of fetal risk. |

TABLE II-continued

PREGNANCY CATEGORY DEFINITIONS

| Category | Definition | Explanation |
| --- | --- | --- |
| B | May be acceptable | Either animal studies show no risk but human studies not available or animal showed minor risks and human studies were done and showed no risk. |
| C | Use with caution if benefits outweigh risks | Animal studies show risk and human studies not available or neither animal nor human studies were done. |
| D | Use in life-threatening emergencies when no safer drug is available | Positive evidence of human fetal risk. |
| X | Do not use in pregnancy | Risks involved outweigh potential benefits. Safer alternatives exist. |

Existing treatment of inflammation focuses on the underlying condition and nature of the presentation. Commonly employed are a myriad of agents such as: diphenhydramine (Benadryl®), oxygen, epinephrine, steroids, beta-agonists, non-steroidal anti-inflammatory agents (NSAIDS), antipyretics, antibiotics, antifungals, and antivirals. Paradoxically, the commonly employed NSAIDS actually increase the production of leukotrienes.

Steroids, which are widely used to treat inflammation, have significant short and long-term side-effects (Table III). With regard to treating inflammation associated with rhinosinusitis, nasal steroids have their limitations, particularly in the elderly and those patients on aspirin, clopidogrel or warfarin prescribed to reduce the risk of stroke and heart attack. Even in patients who do not take these traditional "blood thinners," the risk of spontaneous epistaxis from nasal steroid sprays is between 4-22%. The risk of epistaxis is medication dependent. Epistaxis is a significant consideration in many patients 55 or older.

TABLE III

STEROID SIDE EFFECTS

| Short term | Long term |
| --- | --- |
| Increased propensity for opportunistic infection | Glaucoma |
| Increased blood pressure | Cataracts |
| Mood changes | High-blood pressure |
| Increased blood sugar | Heart disease |
| Increased intraocular pressure | Diabetes mellitus |
| Water retention | Obesity |
| Weight gain | Acid reflux/GERD |
| Increased risk for congestive heart failure | Osteoporosis |
| Flushing | Myopathy |
| Increased appetite | Increased propensity for opportunistic infection |
| Insomnia | Cushing syndrome |

The typical daily dosage for levocetirizine is 5 mg for adults, and levocetirizine exhibits the following advantageous properties: i) Short time to reach peak plasma levels—0.9 hr; ii) Short time to steady state level—40 hrs; iii) Low volume of distribution (goes directly to the target receptor); iv) High receptor occupancy at 24 hours 75%; v) Increased receptor affinity in inflamed tissue (acidic pH; up to 5× that of first generation molecules); vi) Pregnancy category B; vii) FDA approved down to six months for other disease states, i.e., perennial allergic rhinitis and chronic idiopathic urticaria; viii) Anti-inflammatory properties; and ix) Anti-viral properties. Studies in humans have shown that doses of levocetirizine up to 30 mg/day can be safely administered.

Montelukast, a leukotriene receptor antagonist, acts concurrently to protect the respiratory tree as well as block mediators in the inflammatory cascade. The typical daily dosage of montelukast is 10 mg for adults, and montelukast exhibits the following advantageous properties: i) montelukast is a selective receptor antagonist, inhibiting the physiologic action of $LTD_4$ at the $CysLT_1$ receptor; ii) montelukast binds with high affinity and selectivity to the $CysLT_1$ receptor without producing any agonist activity; iii) montelukast is rapidly absorbed; iv) montelukast reaches a peak plasma concentration in 3-4 hours; v) the oral bioavailability and $C_{max}$ of montelukast are not affected by a standard meal; vi) montelukast has a linear pharmacokinetics to 50 mg; vii) doses as low as 5 mg in adults cause substantial blockage of $LTD_4$-induced bronchoconstriction; viii) in a placebo controlled crossover study, montelukast inhibited early-phase bronchoconstriction due to antigen challenge by 75%; ix) montelukast is FDA approved down to six months of age; and x) montelukast has no drug interactions with warfarin, theophylline, digoxin, terfenadine, oral contraceptives, or prednisone. Montelukast has been administered at doses up to 200 mg/day to adult patients for 22 weeks and in short-term studies, and up to 900 mg/day to patients for approximately one week without clinically important adverse experiences.

Accordingly, both levocetirizine and montelukast are pregnancy category B in the United States and are FDA approved in the United States down to six months of age for other disease processes. Moreover, both drugs have only once daily dosing, and no routine monitoring of blood work is necessary for most clinical situations. Further, both drugs exhibit minimal clinically relevant interactions with other medications. As described herein, both levocetirizine and montelukast reach steady state levels within two days to rapidly produce a synergistic and complementary anti-inflammatory effect.

Administration of montelukast and a second generation antihistamine, fexofenadine, has a synergistic effect in the treatment of allergic rhinitis. Allergic rhinitis, also known as pollenosis or hay fever, is an allergic inflammation of the nasal airways which occurs when an allergen such as pollen or dust is inhaled by an individual with a genetically susceptible immune system (estimated at 20 percent of the population). The allergen triggers antibody production, a serum specific immunoglobulin E (IgE), which in turn can bind to mast cells and basophils containing histamine. Upon re-exposure to the offending antigen, histamine is released causing the itching, swelling, and mucus production which are well known to seasonal allergy suffers. A combination of montelukast and fexofenadine reduced nasal congestion both subjectively, using patient diary and VAS evaluations, and objectively, using rhinomanometry and physical examination, with statistical significance compared to fexofenadine alone or fexofenadine with placebo.

However, the scientific literature does not clearly indicate whether the combination of an antihistamine plus a leukotriene offers an advantage over each alone for treatment in general. For example, in one chronic inflammatory disease state, chronic idiopathic urticaria, montelukast did not appear to offer an advantage over the second generation antihistamine desloratadine. See DiLorenzo G, et. al. Randomized placebo-controlled trial comparing desloratadine and montelukast in combined therapy for chronic idiopathic urticaria. J Allergy Clin Immunol 2004; 114-:619-25. Further, the FDA in April 2008 did approve the combination of loratadine, also a second generation antihistamine, and montelukast for the treatment of allergic rhinitis and asthma, finding no benefit from a combined pill.

Here, we describe the unexpected synergistic effects of combining levocetirizine and montelukast. Not wishing to be bound by a particular theory, a detailed examination of the pharmacokinetics of levocetirizine at the cell level illuminates the unique inflammatory properties that extend beyond the IgE mediated release of histamine. Levocetirizine exhibits a low volume of distribution (0.4 L/kg), prolonged dissolution time from the H1 receptor in an acidic ph, enhanced receptor affinity as a pure isomer of cetirizine, and the highest receptor occupancy at 24 hours of any currently available antihistamine. Such parameters impart an inflammatory effect by down regulating IL-4, IL-6, IL-8 as well as cellular adhesion molecules. The later are a homogeneous group of inducible immunoglobulins, integrins and selectins involved in cell-to-cell adhesion, cellular recruitment, homing and healing. In addition levocetirizine has been shown in vivo to decrease ICAM-1, IL-6, IL-8, TLR3 expression and NF-kappa B activation resulting in decreased human rhinovirus titers by log-2. Many rhinovirus serotypes share the same cellular receptor identifying ICAM-1 as the portal of entry into the cell. Levocetirizine inhibits rhinovirus-induced ICAM-1 and cytokine expression and viral replication in airway epithelial cells. One log reduction in viral shedding results in a significant clinical benefit in HRV-infected (human rhinovirus) patients.

An unmet clinical need arose in 2009 with the H1N1 pandemic. The primary drug of choice for influenza, oseltamivir, did not appear to reduce influenza related lower respiratory tract complications. For neuraminidase inhibitors, there was a shortening of the illness by only one half to one day, which indicated that neuraminidase inhibitors do not prevent infection or stop nasal viral excretion, and therefore may be a suboptimal means of interrupting viral spread in a pandemic. Moreover, during this time frame, California reported alarming data on the severity of H1N1 influenza in pregnant and postpartum women, i.e., from Apr. 23 through Aug. 11, 2009 22% of pregnant or postpartum women required intensive care for the treatment of H1N1 and 8% died. Clinically it was demonstrated that the combination of levocetirizine plus montelukast (the latter added to protect the lower airway; both of which were Pregnancy Category B), could be safely and effectively used to ameliorate/shorten the course of influenza.

Not wishing to be bound by a particular theory, the steroid model suggests that levocetirizine acts in a non-IgE-mediated capacity at the level of NF-kB (See FIG. 1) whereas montelukast acts at the CysLT1 receptor to inhibit the physiologic actions of LTD4. Both molecules are known to reduce the quantity of eosinophils or their migration to site of inflammation. Montelukast, in addition, also decreases the recruitment of dendritic cells and T cells.

The actions of levocetirizine plus montelukast surpass the individual physiologic mechanisms of each, well beyond the treatment of allergic rhinitis and asthma. At least in part, it is the anti-viral and anti-inflammatory properties of levocetirizine vis-a-vis nuclear factor kB; the inhibition of the actions of LTD4 by montelukast, underscored by ability of both levocetirizine and montelukast to inhibit the eosinophil quantity/migration, which impart synergy. This synergy is reflected by significantly improved clinical outcomes in a myriad of acute and chronic inflammatory disease states.

Embodiments described herein relate to methods of treating inflammation of the entire respiratory tree, including in part, the nose and paranasal sinuses known as rhinosinusitis with montelukast and levocetirizine. Rhinosinusitis considered on a timeline may be acute, with a duration of less than six weeks (usually 4-6 weeks), subacute, having a duration of six to twelve weeks, or chronic, having a duration of greater than or equal to twelve weeks. Acute rhinosinusitis may be precipitated by multiple factors not limited to chemical irritation, trauma, allergic rhinitis or an earlier upper respiratory tract infection, which may be bacterial, viral, or, less commonly, fungal in origin. The most common causative agents of acute sinusitis of bacterial origin are *Streptococcus pneumoniae, Haemophilus influenzae, Moraxella catarrhalis, Staphylococcus aureus*, other streptococci species, anaerobic bacteria, and, less commonly, gram negative bacteria. Bacterial sinusitis tends to be more persistent than viral rhinosinusitis, i.e., the common cold, which typically lasts for 7 to 10 days.

Several embodiments described herein relate to the treatment of acute rhinosinusitis caused by a viral or bacterial infection with montelukast and levocetirizine. In some embodiments, montelukast and levocetirizine are taken prophylactically to prevent a viral respiratory tract infection from escalating to an acute, often opportunistic, secondary bacterial sinusitis, bronchitis and/or pneumonia. In some embodiments, montelukast and levocetirizine are administered immediately, one hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, and/or 30 days after exposure to the pathogens (virus, bacteria, fungi, etc.). Several embodiments relate to the treatment of patients with clinical manifestations of influenza with montelukast and levocetirizine. In some embodiments, montelukast and levocetirizine treatment reduces the duration of influenza. In some embodiments, montelukast and levocetirizine treatment reduces the severity of influenza symptoms. Several embodiments relate to the treatment of patients with clinical manifestations of the common cold with montelukast and levocetirizine. In some embodiments, montelukast and levocetirizine treatment reduces the duration of the cold. In some embodiments, montelukast and levocetirizine treatment reduces the severity of cold symptoms.

Chronic rhinosinusitis is an inflammatory condition/disease of the nose and paranasal sinuses lasting for greater than or equal to twelve weeks. Symptoms include in part, any combination of nasal congestion, facial pain, headache, coughing, an increase in asthma symptoms, malaise, discharge, feeling of facial tightness, dizziness, and/or aching teeth. Rhinosinusitis in general can be categorized into four categories: (1) acute bacterial rhinosinusitis (ABRS), (2) chronic rhinosinusitis without nasal polyposis (CRSsNP), (3) chronic sinusitis with nasal polyposis (CRSwNP), and (4) allergic fungal rhinosinusitis (AFRS). See Meltzer, E O. Rhinosinusitis: Developing guidance for clinical trials. J Allergy Clin Immunol 2006 November; S20. Nasal polyposis is a subgroup of chronic rhinosinusitis in which the inflammation of the nose is associated with two or more of the following signs and symptoms: nasal obstruction or congestion, nasal discharge, hyposmia or anosmia, facial pain or feeling of pressure, endoscopic evidence of polyps or mucopurulent discharge from middle meatus with or without edema or mucosal obstruction of the meatus and CT images which show mucosal changes of osteomeatal complex or paranasal sinuses. See Fokkens W, et. al. EAACI position paper on rhinosinusitis and nasal polyps executive summary. Allergy, 2005; 60, 583-601, Fokkens, W, et. al. European Position Paper on Rhinosinusitis and Nasal Polyps group (2007) European position paper on rhinosinusitis and nasal polyps. Rhinology 2007; 20, 1-136. Conventional treatment for chronic rhinosinusitis often involves functional endoscopic sinus surgery, antibiotics, systemic and topical steroids, and to a much lesser extent an antihistamine or leukotriene modulator. The use of antihistamines in patients with only polyps has not been extensively studied. See Casale M, et. al. Nasal Polyposis: From Pathogenesis to Treatment, an Update. Inflammation & Allergy—Drug Targets 2011, 10, 158-163. Mometasone furoate monohydrate, a topical nasal steroid spray, is the only FDA approved medication in the United States for the treatment of nasal polyposis. The recommended dose is two squirts each nostril twice a day.

Embodiments described herein relate to the treatment of chronic rhinosinusitis with montelukast and levocetirizine. Several embodiments described herein relate to the treatment of nasal polyposis with montelukast and levocetirizine. In some embodiments, montelukast and levocetirizine treatment reduces the size and/or number of polyps. Some embodiments relate to the treatment of chronic rhinosinusitis with montelukast and levocetirizine in the absence of steroids, antibiotics or surgical treatment. In other embodiments, montelukast and levocetirizine are administered in conjunction with antibiotics and/or steroids and/or surgical treatment as deemed clinically applicable. The chronic rhinosinusitis treatment protocol with or without other treatment modalities is as follows:

TABLE IV

TREATMENT PROTOCOL FOR CHRONIC RHINOSINUSITIS

| Levocetirizine - US | |
|---|---|
| Adults: | 5 mg/day |
| Children: 6-11 years of age: | 2.5 mg/day |
| Children: 6 months to 5 years | 1.25 mg/day |
| Montelukast - US | |
| Adults: | 10 mg orally/day |
| Children 6-14 years of age: | 5 mg orally/day |
| Children 6 months-5 years of age: | 4 mg orally/day |

Patients may be seen at least quarterly in the office with endoscopic review of the nose/paranasal sinuses when clinically appropriate. A pretreatment and follow-up CT scan of the perinasal sinuses at 6 months to one year post initiation of therapy may be performed to provide objective data on which to tailor existing medical therapy.

Several embodiments relate to a method of treating rhinitis with montelukast and levocetirizine. Rhinitis, inflammation of the nasal passages, is commonly caused by a viral or bacterial infection, including the common cold, the latter of which is caused primarily by Rhinoviruses and Coronaviruses. See Eccles R. Understanding the Symptoms of the Common Cold and Influenza. Lancet Infectious Diseases 2005; 5(11): 718-725. Rhinitis is categorized as: (i) infective rhinitis; (ii) nonallergic rhinitis; and (iii) allergic rhinitis. Several embodiments relate to a method of treating infective rhinitis with montelukast and levocetirizine. Some embodiments relate to a method of treating nonallergic rhinitis with montelukast and levocetirizine. Some embodiments relate to a method of treating allergic rhinitis with montelukast and levocetirizine.

Several embodiments described herein relate to the treatment of chronic rhinosinusitis with montelukast and levocetirizine. Some embodiments, relate to the treatment of chronic rhinosinusitis with montelukast and levocetirizine in the absence of steroid or antibiotic treatment. In other embodiments, montelukast and levocetirizine are administered in conjunction with antibiotics and/or steroids.

Several embodiments relate to a method of treating non-IgE-based inflammation with montelukast and levocetirizine. Example 5 presents the case study of a 90 year old male presenting with CRSsNP with associated cough and post nasal drainage as an example of successfully treating a non-IgE-mediated inflammatory response with a combination of montelukast and levocetirizine.

Several embodiments relate to a method of treating combined IgE and non-IgE-mediated inflammation with montelukast and levocetirizine. Example 6 presents the case study of 78 year old female with CRScNP resulting in a loss of taste and smell as an example of successfully treating combined IgE and non-IgE-mediated inflammation with a combination of montelukast and levocetirizine.

The following Table V shows the existing country guidelines for dosages in the treatment of allergic disorders.

TABLE V

GUIDELINES FOR DOSAGES IN THE TREATMENT OF ALLERGIC DISORDERS

| Levocetirizine - US | |
|---|---|
| Adults: | 5 mg/day |
| Children: 6-11 years of age: | 2.5 mg/day |
| Children: 6 months to 5 years | 1.25 mg/day |
| Montelukast - US | |
| Adults: | 10 mg orally/day |
| Children 6-14 years of age: | 5 mg orally/day |
| Children 6 months-5 years of age: | 4 mg orally/day |

Several embodiments relate to the use of a combination of levocetirizine and montelukast to treat a bacterial infection. Examples of bacterial infections that may be treated by a combination of levocetirizine and montelukast include, but are not limited to, acute bacterial rhinosinusitis (ABRS). In some embodiments, levocetirizine and montelukast may be administered with an antibiotic as determined by local presentation.

Several embodiments relate to the use of a combination of levocetirizine and montelukast to treat otitis media with effusion and associated ear disorders such as chronic mastoiditis and eustachian tube dysfunction (the auditory tube leading from the back of the nose to the middle ear). In some embodiments, levocetirizine and montelukast may be administered with antibiotics to treat for example, acute otitis media with purulent middle ear effusion. In some embodiments, levocetirizine and montelukast may be administered without antibiotics to treat chronic middle ear effusion, for example, chronic otitis media. In some embodiments, levocetirizine and montelukast may be administered with other treatment modalities such as, but not limited to, steroids and/or antiviral agents.

Several embodiments relate to the use of a combination of levocetirizine and montelukast to treat allergic fungal rhinosinusitis (AFRS). In some embodiments, levocetirizine and montelukast may be administered with other treatment modalities such as, but not limited to, steroids and/or an antifungal agent.

Intravenous therapy of levocetirizine and montelukast, the latter currently under investigation in the United States, would enhance the individual and combined clinical response presently seen with the administration of oral medication. The IV montelukast plasma concentration area under the curve profile, 7 mg, is comparable to the approved 10 mg oral montelukast tablet. The former has been shown in acute asthmatics to significantly improve FEV1 (forced expiratory volume at one sec) at 10 minutes when compared with placebo.

Accordingly, the dosing for acute inflammation could be daily as delineated above individually in the same setting, as a dual-layer tablet(s), and/or as a blister pack containing both medications for a 10 day course of therapy. For a moderate to severe clinical presentation, the levocetirizine component can be given at time zero (5 mg), 12 hours (5 mg) and 24 hours (5 mg), during the first 24 hour day, in order to achieve a steady state level of the molecule in less than 40 hours. Levocetirizine human dosing safety studies have been performed at up to 30 mg/day. Sedation is the principal side effect experienced at higher doses. Independent research has shown that levocetirizine alone can be dosed at 20 mg/day to treat severe cases of idiopathic urticaria.

The application for the combination of levocetirizine and montelukast includes, but is not limited to treating, ameliorating, or preventing the following symptoms. For Influenza, the combination can be useful to shorten the course of seasonal flu and prevent or minimize the development of lower respiratory tract infections/complications, and/or to establish an improved, safe, world-wide protocol for influenza prior to the next pandemic, e.g., H5N1 with its associated 50% mortality rate. For upper respiratory tract infections, not limited to rhinovirus, the combination can be useful to limit the infection itself, and/or to prevent or reduce the potential development of secondary sinusitis, bronchitis and pneumonia. The combination can be useful for treatment of Ebstein-Barr Virus, particularly, but not limited to those patients with respiratory involvement.

For acute asthma in conjunction with existing protocols, not limited to exacerbations caused by rhinovirus (~50% of cases), the combination can be useful to shorten the course of the event, reduce hospitalizations and death. The combination can be useful for pre-treatment of patients allergic to one or more classes of antibiotics requiring antimicrobial therapy. These patients are at risk, 4-10× over the general population, of developing a subsequent ALE (allergic-like event). For patients with moderate to severe life-threatening disease requiring dual/triple antibiotics, the combination can be useful to reduce the probability of developing a side-effect(s) from the primary treatment medications. The combination can be useful during and following radiation therapy to ameliorate the inflammatory response. The combination can be useful for patients requiring steroids for the treatment of inflammation who are otherwise at increased risk for the development of steroid induced complications. Examples include but are not limited to the following: i) A severe insulin dependent diabetic with an infection such as facial paralysis, and ii) Patient with latent Tuberculosis. For patients on antiviral medication for acute disease, the combination can be used to prevent complications related to the medication(s) as well as complications associated with the disease process itself. The combination can be used to treat serum sickness, with or without steroids. For pre-treatment of patients on immunotherapy, the combination can be used to prevent or ameliorate the risk of a systemic reaction. Examples of high risk patients with the potential to develop a life-threatening, systemic event include but are not limited to severe asthmatics, those patients with a concurrent respiratory tract infection, and those patients with a prior history of a systemic reaction. For pre and intra-treatment of those patients on chemotherapy, the combination can be used to ameliorate side effects associated with the administration of chemotherapeutic drug(s). For patients exhibiting a transfusion reaction, the combination can be used to limit the side effects/life threatening event during the initial reaction and in preparation for any requisite subsequent transfusion.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

TABLE VI

TREATMENT PROTOCOL FOR ACUTE INFLAMMATION NOT LIMITED TO INFLUENZA AND THE COMMON COLD

| Levocetirizine - US | |
| --- | --- |
| Adults: | 5 mg/day |
| Children: 6-11 years of age: | 2.5 mg/day |
| Children: 6 months to 5 years | 1.25 mg/day |
| Montelukast - US | |
| Adults: | 10 mg orally/day |
| Children 6-14 years of age: | 5 mg orally/day |
| Children 6 months-5 years of age: | 4 mg orally/day |

Depending upon the severity of the acute process, the doses in Table VI can be modified. For example, the age appropriate dose for levocetirizine may be given at time zero (at presentation) with an additional age appropriate dose at 12 hours. In order to protect the lower airway, particularly in the face of bronchitis/pneumonia, a dose of montelukast may be given at time zero (at presentation) with an additional age appropriate dose of montelukast at 12 hours. In this fashion the steady state level of the two drugs would approach 24 hours. Montelukast, like levocetirizine, is considered a very safe molecule. Montelukast has been administered at doses up to 200 mg/day (20× the standard adult daily dose) to adult patients for 22 weeks and in short-term studies, up to 900 mg/day (90× the standard adult daily dose) to patients for approximately one week without clinically important adverse events. Dosing duration may parallel the generally accepted protocols for their respective disease states. For example, conventional therapy for an acute infectious disease process is typically administered for 5-14 days. A course of combined levocetirizine once daily plus montelukast once daily may be given for the same duration. For the treatment of chronic inflammatory disease states, an age appropriate once daily dosing of each medication may also be administered.

The term "effective amount" includes an amount effective, at dosages and for periods of time necessary, to achieve the desired result, e.g., sufficient to treat influenza, common cold, or acute, subacute, and chronic inflammation in a patient or subject. An effective amount of levocetirizine and montelukast may vary according to factors such as the disease state, age, and weight of the subject, and the ability of levocetirizine and montelukast to elicit a desired response in the subject. Dosage regimens may be adjusted to provide the optimum therapeutic response. An effective amount is also one in which any toxic or detrimental effects (e.g., side effects) of levocetirizine and montelukast are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with levocetirizine and montelukast, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of respiratory or inflammatory disorders in a subject, and/or by modalities such as, but not limited to photographs, video, digital imaging and pulmonary function tests. Amelioration may be transient, prolonged or permanent or it may be variable at relevant times during or after levocetirizine and montelukast are administered to a subject or is used in an assay or other method described herein or a cited reference, e.g., within timeframes described infra, or about 1 hour after the administration or use of levocetirizine and montelukast to about 28 days, or 1, 3, 6, 9 months or more after a subject(s) has received such treatment.

The "modulation" of, e.g., a symptom, level or biological activity of a molecule, or the like, refers, for example, to the symptom or activity, or the like that is detectably increased or decreased. Such increase or decrease may be observed in treated subjects as compared to subjects not treated with levocetirizine and montelukast, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and pulmonary function tests. Modulation may be transient, prolonged or permanent or it may be variable at relevant times during or after levocetirizine and montelukast are administered to a subject or is used in an assay or other method described herein or a cited reference, e.g., within times described infra, or about 1 hour after the administration or use of levocetirizine and montelukast to about 3, 6, 9 months or more after a subject(s) has received levocetirizine and montelukast.

As used herein, the terms "prevent," "preventing," and "prevention" refer to the prevention of the recurrence, onset, or development of influenza, common cold, and acute, subacute, and chronic inflammation. Preventing includes protecting against the occurrence and severity of upper and/or lower respiratory tract infections.

As used herein, the term "prophylactically effective amount" refers to the amount of a therapy (e.g., a pharmaceutical composition comprising montelukast and levocetirizine) which is sufficient to result in the prevention of the development, recurrence, or onset of influenza, common cold, and acute, subacute, and chronic inflammation or to enhance or improve the prophylactic effect(s) of another therapy.

As used herein, "subject" includes organisms which are capable of suffering from influenza, common cold, and acute, subacute, and chronic inflammation or other disorder treatable by a combination of montelukast and levocetirizine or who could otherwise benefit from the administration of montelukast and levocetirizine as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc.

The following Examples are presented for the purposes of illustration and should not be construed as limitations.

EXAMPLES

Example 1

Case Study 1:

Young Adult Male (13 years; Wt—68 kg) with Influenza.

The patient had depressed white blood cell count of 2.3K and was treated with the combination of levocetirizine and montelukast as described below.

Symptoms/signs: Extreme fatigue, cough, fever, myalgias, nasal congestion, chills, and night sweats. Past medical history: allergic rhinitis, asthma.

| Chronology | |
|---|---|
| Day 1 | Fatigue |
| Day 4 | Fatigue |

-continued

| | |
|---|---|
| Day 6 | Fatigue, fever, sweats, chills |
| Day 9-Day 10 | Fatigue, dry hacking cough, fever, chills, nasal congestion, myalgias |
| Day 10 | Therapy initiated<br>levocetirizine - 5 mg<br>montelukast - 10 mg<br>naproxen for fever, myalgias<br>phenergan with codeine<br>amoxicillin/beta-clavulanic acid - 875 mg<br>Initial office examination |
| Day 11 | T - 96 tympanic (on naproxen 220 mg) pulse 84 respiratory rate 12<br>Complaining and exhibiting extreme fatigue, dry cough, myalgias<br>Ears: tympanic membranes gray<br>Nose: blocked airway on the left 2.75+ yellow secretions (double cultured)<br>Throat: mild oropharyngeal erythema<br>Neck: without adenopathy<br>Lungs: scattered rales<br>Heart: S1 S2 distinct, regular rhythm, no murmur<br>Influenza - r/o secondary bacterial infection<br>Labs - CBC/Comprehensive metabolic panel/C-reactive protein<br>Double culture of the nasopharynx for aerobes/additional nasopharyngeal swab for influenza A/B<br>Chest X-ray - AP and lateral |

Medications

| | |
|---|---|
| levocetirizine | 5 mg po hs |
| montelukast | 10 mg po hs |
| amoxicillin/beta-clavulanic acid prophylaxis | 875 mg po bid × 10 days to cover potential strep pneumoniae and haemophilus influenza as opportunistic secondary pathogens, oxymetazoline nasal spray - bid × four days to improve ventilation of the upper airway (strep pneumoniae and haemophilus influenza are faculative anaerobes) |
| naproxyn sodium | 220 mg po, bid, prn, fever, myalgia |
| Kefir ® (probiotic) | 3 oz with 3 ounces of yogurt bid, to decrease the propensity of gastrointestinal side effects from the antibiotic |
| mupirocin cream | applied to the nasal inlets via q-tip bid to suppress potential Staph Aureus as an opportunistic pathogen |
| phenergan with codeine | 5 cc po q 4 hours, prn, cough |

Clinical course

| | |
|---|---|
| Day 11 | White blood cell count - 2.3k, low [normal 4-10k], compatible with a viral infection<br>Cultures negative - clinically insignificant normal respiratory flora, scant enterics, very scant non methicillin resistant Staph Aureus<br>Chest x-ray - no infiltrate |
| Day 13 | White blood cell count - 2.6k, still suppressed<br>Lymphocytes 64.8% high [normal 15-48]<br>Neutrophils 24.5% low [normal 40-75]<br>Natural killer cells 3% low [normal 4-14] |
| Day 18 | White blood cell count - 5.8k, returned to normal |

The patient had significantly responded to therapy at ~67 hours from initiation of therapy, i.e., no complaints: no fever, no myalgias, no fatigue.

Concurrent provider—pulmonary medicine/no additional recommendations or therapy.

Clinical outcome—Complete resolution of the disease process without complications.

Example 2

Case Study 2:

Viral Infection by Clinical Presentation/Culture Negative for Strep.

An eight-year-old male with salient medical history of seasonal allergic rhinitis was treated with the combination of levocetirizine and montelukast as described below.

Chronology

| | |
|---|---|
| Day 1 | Symptom onset 12 hours earlier<br>Rapidly increasing<br>PM, Temp: 102.4 tympanic Weight: 78#/HT: 54"<br>Fatigue - significant<br>Congestion - mild<br>Sore throat - low grade<br>Mild cervical lymphadenopathy<br>Decreased appetite<br>Non-productive cough<br>Therapy initiated<br>levocetirizine - 2.5 mg po hs/syrup<br>montelukast - 5 mg po hs/chewable tablet<br>acetaminophen - 160 mg/S cc - 12.5 cc po alternating with ibuprofen (100 mg/5 cc), 12.5 cc, po, q 4-6 hours, prn, fever |
| Day 2 | Throat culture - negative<br>Therapy |

| Chronology | |
|---|---|
| | levocetirizine - 2.5 mg po am and pm
montelukast - 5 mg po hs
acetaminophen - 160 mg/5 cc - 12.S cc po alternating with
ibuprofen (100 mg/5 cc), 12.5 cc, po, q 4-6 hours, prn,
fever |
| Day 3 | Therapy
levocetirizine - 2.5 mg po hs
montelukast - 5 mg po hs |
| Day 4 | AM, Symptoms had clinically resolved at 2.5 days from the
initiation of therapy |

Example 3

Case Study 3:

76-year-old Adult Male with acute on chronic moderate to severe rhinosinusitis. Prior to Day 1, this patient with rhinosinusitis was previously treated with a month of Augmentin® (amoxicillin/clavulanate; amox/clav) and six weeks of oral steroids by his pulmonary medicine physician.

| Chronology | |
|---|---|
| Day 1 | Severe coughing 25-30 times a day
Ears: (10x) gray tympanic membranes, no middle ear effusions
Nose: 2+ moisture content, mild erythema, no purulence noted |
| | Throat: relatively long uvula with respect to the craniofacial
profile, otherwise normal
Neck: without adenopathy
Laryngoscopy with photography: mild erythema of the intrinsic
larynx and vocal cords, bowing of the true vocal cords, no
mass lesion seen
Total serum IgE - 335, significantly elevated as an index for
allergy
Therapy initiated
levocetirizine - 5 mg po hs
montelukast - 10 mg po hs |
| Day 29 | Complete recovery/complete resolution of the severe cough
No complications |

Example 4

Case Study 4:

74-year-old Adult Male with acute on chronic disease.

| Initial office examination | |
|---|---|
| Day 1 | Severe nocturnal paroxysmal coughing underscored by
pneumonia (bilateral lower lobe)
Asthma
Allergic rhinitis (Total IgE - 366; normal 0-60)
Marked esophagitis
Double aortic arch with complete ring
Chronic rhinosinusitis
Exertional shortness of breath,
Nasal congestion
Coryza
Ears: (10x) gray tympanic membranes, no middle ear effusions
Nose: endoscoped and photographed - mild erythema of the
mucosa, polypoid changes noted, posterior septal perforation,
elevated 2.75+/4+ moisture content
Throat: status post tonsillectomy
Neck: without adenopathy
Laryngoscopy with photography: significant clear to yellow
drainage noted, erythema of the cords and posterior commissure
with polypoid changes posteriorly on the left vocal cord |
| Medications | |
| mometasone nasal spray | 2 puffs each nostril bid |
| azelastine nasal spray | 2 puffs each nostril bid |
| montelukast | 10 mg po hs |
| fluticasone/salmeterol | 500/50 one puff bid |
| prednisone | ten-day taper initiated |
| moxifloxacin | 400 mg po qd |
| latanoprost and brimonidine eye drops | each eye qd |
| simvastatin | 20 mg po qd |
| esomeprazole | 40 mg po qd |
| enalapril | 5 mg po qd |
| finasteride | 5 mg po qd |
| Added to the treatment regimen | |
| levocetirizine | 5 mg po hs |
| lorazepam | 0.5 mg po hs later replaced with diazepam one
mg at dinner, ultimately discontinued |
| guaifenesin | 100 mg/5 cc, 15-20 ml, 3-4x/day, ultimately
tapered to 15 ml po hs |
| Daily nasal irrigation | |
| Allergy environmental control | |

Clinical outcome—complete resolution of the problem with stabilization of the inflammatory airway and esophageal disease/no complications.

This is an example of how combination therapy can be added to existing protocols to safely and effectively treat a complex medical problem.

Example 5

Case Study 5:

90-year-old man presenting with chronic rhinosinusitis without nasal polyposis (CRSsNP).

Chronology

Day 1: Patient presented with a history of a cough, frequent throat clearing, post nasal drainage and headache. Headache was described as low grade pressure scaled 2 3/10 in the midface and frontal region, intermittent in character and occurring in a frequency of approximately once per week. Patient was taking no medications other than Vitamin A, D3, COQ10 and fish oil. Patient was a non-smoker who tested negative for allergic rhinitis. Inflammation was a non-IgE-mediated response to chronic rhinosinusitis without nasal polyposis. The patient was not a candidate for functional endoscopic sinus surgery and oral steroids were contraindicated due to the patient's age and the numerous side effects associated with steroid use.

Therapy:

Montelukast 10 mg po at bedtime.

Day 56: Patient reported improved breathing, but congestion "further back in the nose."

Therapy:

montelukast 10 mg po at bedtime.

Day 224: Patient complained of continuous post nasal drainage.

Therapy:

Montelukast 10 mg po at bedtime.

Samples of levocetirizine 5 mg po at hs (#7) to be taken with the montelukast at bedtime.

Day 258: Patient reported symptoms unchanged. Patient had stopped the medications after running out of the samples of levocetirizine and thirty day prescription for montelukast.

Figures 2A, 2C:
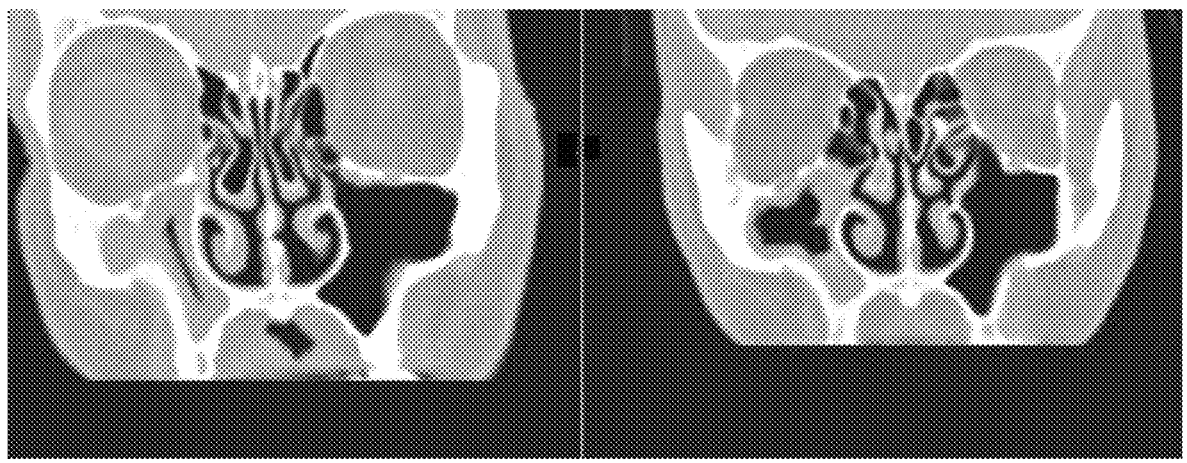
FIGS. 2A-D show digital radiographic CT images taken through the mid aspect of the nose and paranasal sinuses of a ninety year old male presenting with chronic rhinosinusitis without nasal polyposis (CRSsNP) (See Example 5).
Figures 2B, 2D:

Therapy: Combination Therapy Re-Discussed levocetirizine 5 mg po hs montelukast 10 mg po hs Vitamins D3, A, CoQ10, fish oil and Vitamin B12 sublingual Day 371: CT scan of the paranasal sinuses to compare with baseline image (FIG. 2C and FIG. 2D) documented a significant improvement (decrease) in mucosal thickening in right maxillary sinus visualized as decreasing areas of gray on the left side of each sinus image. Clinically the patient had no facial pressure, less post nasal drainage and less cough at the time of follow-up. Side effects-none. He expressed a desire to continue the combined treatment regimen.

Pertinent Physical Examination (Serial Exams):

Ears: 2+ tympanosclerosis right, 1+ left, no infection, cholesteatoma or middle ear effusions Nose: right deviated nasal septum Throat: mild erythema of the vocal cords secondary to post nasal drainage Nasopharynx: post nasal drainage, no tumor or obstruction seen Neck: without adenopathy Outcome: resolving inflammatory airway disease/complications—none: Treatment ongoing with anticipated complete resolution at eight months to one year from the initiation of therapy.

Example 6

Case Study 6:

78-year-old female presenting with chronic rhinosinusitis with nasal polyposis (CRSwNP) resulting in the loss of taste and smell.

Chronology

Figure 3A:
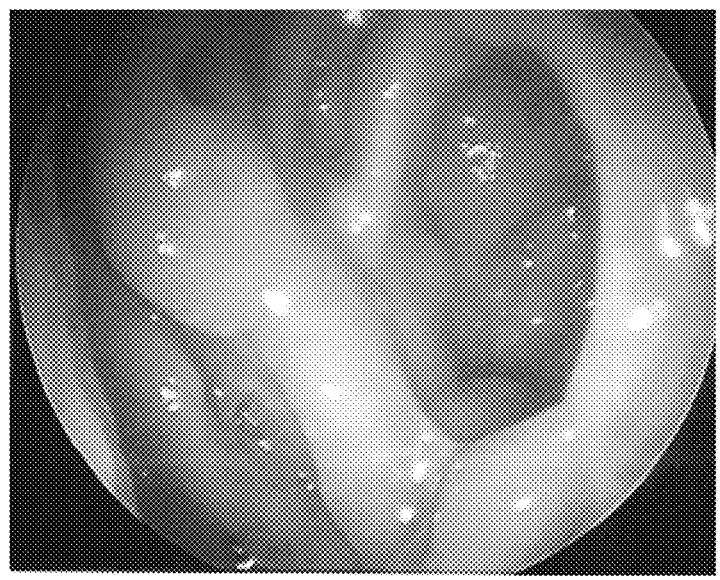
FIGS. 3A-C show endoscopic photographs taken during the course of treatment of a seventy-seven year old female patient with chronic rhinosinusitis with nasal polyposis (CRSwNP) manifested as a loss of sense of taste and smell (See Example 6).

Day 1: Patient with a history of chronic rhinosinusitis, asthma and allergic rhinitis complained at presentation of loss of the sense of taste and smell. This is an example of a combined non-IgE-mediated as well as IgE-medicated response in a patient with chronic rhinosinusitis with nasal polyposis, atopic asthma and allergy. Patient had undergone functional endoscopic sinus surgery by another physician approximately ten years earlier. Patient was taking maintenance medication, which included fluticasone 250/salmeterol 50 twice a day for asthma as well as the periodic use of fluticasone nasal spray. Endoscopic photographs show the presence of nasal polyps. See FIG. 3A. At this juncture levocetirizine 5 mg orally once a day and montelukast 10 mg once a day was added to the treatment regimen.

Day 4: A CT scan of the sinuses documented prior bilateral nasoantral windows with partial resection of the middle turbinates. Mucosal thickening involved the paranasal sinuses, most significantly the left maxillary sinus.

Therapy:

levocetirizine 5 mg po hs montelukast 10 mg po hs

Figure 3B:

Preexisting Medications:

Advair® (fluticasone/salmeterol 50/250 discontinued during treatment albuterol discontinued during treatment fluticasone nasal spray discontinued during treatment Cymbalta® (duloxetine) 60 mg po qd omeprazole 20 mg po qd lorazepam 1 mg po qd Day 148: Patient reported that her sense of smell and taste had returned after approximately two months of use of the levocetirizine+montelukast, each taken once daily. Patient also reported that she stopped using her Advair® (fluticasone/salmeterol) 250/50 two months prior to the most recent visit and her albuterol rescue inhaler one month later. Photographs were taken of the left maxillary sinus depicting a significant decrease in mucosal swelling. See FIG. 3B.

Figure 3C:
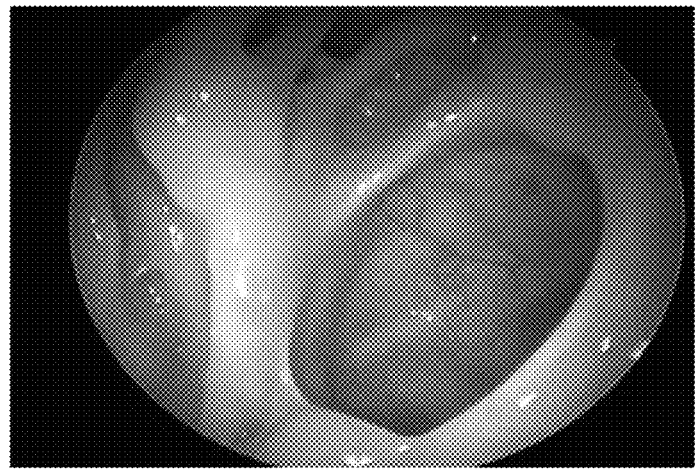

Day 323: Patient exhibited continued and significant improvement in the intranasal and maxillary sinus mucosa. The patient has regained her sense of taste and smell since the initiation of levocetirizine and montelukast and has experienced no interval respiratory tract infections. Endoscopic photographs show the respiratory mucosa and associated intranasal and paranasal sinus anatomy is returning to normal. See FIG. 3C. Therapy is ongoing.

Pertinent Physical Examination (Serial Exams):

Ears: gray tympanic membranes, normal landmarks

Nose: polypoid mucosal changes documented with the endoscope/photography

Throat: normal oropharynx status post tonsillectomy

Neck: well healed scar right neck

Outcome: resolving chronic inflammatory airway disease/ restoration of sense of taste and smell; improved control of atopic asthma and allergy/no interval infections or exacerbations of asthma/improved quality of life/no complications.

Example 7—Synergistic Effects of Administering Levocetirizine in Conjunction with Montelukast for the Treatment of Influenza Based on the inventor's clinical experience using levocetirizine and montelukast, the following results are expected in a controlled study. A cohort of 20 patients between the ages of 15-30 years of age (and no other co-morbid disease processes), presenting with classic symptoms of influenza: headache, fever, dry cough and extreme fatigue, are identified and divided into four treatment groups. The first group (CONTROL) receives two placebo tablet(s) each administered together at the same time each day for a period of 10 days. The second group (LEVO) receives levocetirizine—5 mg po and a placebo tablet simultaneously at the same time each day for 10 days. The third group (MONT) receives montelukast—10 mg po and a placebo tablet simultaneously at the same time each day for 10 days. The fourth group (COMBO) receives levocetirizine—5 mg po and montelukast—10 mg po simultaneously for 10 days.

CONTROL patients exhibit a 'normal' course of influenza with symptoms persisting for 7-10 days. Laboratory data shall consist of a complete blood count, comprehensive metabolic panel, C-reactive protein, T and B cell lymphocyte panel, chest x-ray, and viral and aerobic cultures of the airway. Vital signs will be logged at the initial visit and the patient's fever profile tracked over the interim. Onset, duration and intensity of symptoms (headache, fever, cough, fatigue) will be logged in addition to the time to resolution of symptoms (time zero-first dose of medication(s)). Second endpoint data will include the time it takes to return to full activity, work/school.

LEVO patients exhibit a reduced fever profile and overall feeling of fatigue, without significant foreshortening of the disease process.

MONT patients exhibit an improvement in the symptoms of congestion and shortness of breath.

COMBO patients exhibit an amelioration of symptoms and an overall foreshortening of the disease process by greater than 3 days. Patients show limited/no disease pathology after 3-5 days, compared to 7-10 days for CONTROL, LEVO and MONT.

The results are consistent with a synergistic effect of the combination.

Example 8—Testing the Synergistic Effects of Administering Levocetirizine in Conjunction with Montelukast for the Treatment of Rhinovirus A cohort of 100 non-atopic healthy volunteers who test negative for human rhinovirus 16 (HRV-16) is identified for participation in a randomized, double-blind, placebo-controlled trial designed to test whether treatment with levocetirizine and montelukast would lessen duration and/or severity of rhinitis symptoms associated with experimental inoculation with HRV-16. Peak flow meters are issued to participants at the beginning of the study and participants are asked to fill out peak flow and cold symptom diaries daily for 7 days before randomization, 7 days before inoculation, and then 14 days after inoculation. Nasal lavage, sputum, and blood specimens are collected from the participants at baseline, during the acute cold phase, and on recovery.

The Jackson scale is used to assess the 13 cold symptoms (cough, nasal discharge, sneezing, stuffy nose, sore throat, headache, malaise, chilliness, shaking chills, fever, laryngitis, aching joints or muscles, and watery or burning eyes) on a 4-point scale (0, not present; 1, mild; 2, moderate; and 3, severe). The symptoms are scored twice daily, for the duration of the study and the highest value for each symptom is used to calculate the total daily highest symptom score (TDHSS; maximum possible daily score of 39).

The participants are randomized and divided into four treatment groups. The first group (CONTROL) receives two placebo tablet(s) each administered together at the same time each day for the duration of the study. The second group (LEVO) receives levocetirizine—5 mg po and a placebo tablet simultaneously at the same time each day for duration of the study. The third group (MONT) receives montelukast—10 mg po and a placebo tablet simultaneously at the same time each day for duration of the study. The forth group (COMBO) receives levocetirizine—5 mg po and montelukast—10 mg po simultaneously for duration of the study.

All participants are inoculated with HRV-16 simultaneously with the initiation of the study medications/placebos. Samples taken on the day of inoculation are analyzed by multiplex polymerase chain reaction (PCR) for the presence of other respiratory viruses.

Viral titers from nasal lavage are calculated after 4 tissue culture tubes containing WI38 cells (human lung diploid cells; ViroMed, Minnetonka, Minn.) are inoculated for each serial 10-fold dilution of sample ($10^0$-$10^{-7}$) and incubated while rolling at 33° C. for 10 days. Tubes are read at 24 hours and then every other day up to day 10. $TCID_{50}$ are calculated as the concentration that is capable of infecting 50% of the tubes. Viral titers are expressed as $TCID_{50}$ per milliliter. Total RNA is extracted from nasal lavage samples and reverse transcribed, and the quantity of HRV RNA is measured.

Outcomes, including peak flow, sputum and nasal cell counts and percentages, cold symptom scores, viral shedding and RNA, will be compared using the Wilcoxon rank sum test. Categorical outcomes, including detection of nasal eosinophils will be compared using the Fisher exact test. For daily-recorded data (symptom scores), both the mean and maximum will be calculated for each of 4 study weeks (baseline, randomization, acute phase, convalescent phase) and compared between groups. Continuous outcomes are summarized as median (interquartile range [IQR]). A 2-sided $P<0.05$ is regarded as statistically significant.

Based on the inventor's clinical experience using levocetirizine and montelukast, the following results are expected in a controlled study.

CONTROL patients are expected to exhibit a 'normal' course of the common cold with symptoms persisting for 7-10 days.

LEVO patients are expected to exhibit a mild to moderate reduction of the common cold symptoms (TDHSS) without appreciably foreshortening the duration of the overall disease process.

MONT patients exhibit an improvement in the symptoms of cough and congestion.

COMBO patients are expected exhibit an amelioration of symptoms and an overall foreshortening of the disease process by greater than 3 days. Patients are expected to show limited/no disease pathology at 3-5 days post inoculation of HRV, compared to 7-10 days for CONTROL, LEVO and MONT.

Example 9—Testing the Synergistic Effects of Administering Levocetirizine in Conjunction with Montelukast for the Treatment of Chronic Rhinosinusitis with Nasal Polyposis (CRSwNP)

A cohort of volunteers diagnosed with CRSwNP is identified for participation in a randomized, double-blind, placebo-controlled trial designed to test whether treatment with levocetirizine and montelukast would lessen the number and size of nasal polyps and symptoms associated with chronic rhinosinusitis. At the beginning of the study each participant receives: (1) a baseline CT Scan of the perinasal sinuses, (2)

endoscopic evaluation of the nose with photographs, and (3) a standardized disease specific quality of life (QOL) questionnaire such as the rhinoconjunctivitis quality of life questionnaire.

The participants are randomized and divided into four treatment groups. The first group (CONTROL) receives two placebo tablet(s) each administered together at the same time each day for the duration of the study. The second group (LEVO) receives levocetirizine—5 mg po and a placebo tablet simultaneously at the same time each day for duration of the study. The third group (MONT) receives montelukast—10 mg po and a placebo tablet simultaneously at the same time each day for duration of the study. The forth group (COMBO) receives levocetirizine—5 mg po and montelukast—10 mg po simultaneously for duration of the study.

For a duration of 12 months, participants are evaluated every two months. Endoscopic photographs are taken of the participants' nasal passages to document the number and size of nasal polyps and the level of inflammation. Quality of life questionnaires are repeated. At completion of the study the following are obtained on each participant: (1) follow-up CT scan of the perinasal sinuses to compare with the baseline examination, (2) endoscopic photographs, and (3) the final QOL questionnaire.

Based on the inventor's clinical experience using levocetirizine and montelukast, the following results are expected in a controlled study.

CONTROL patients are expected to exhibit limited to no improvement in the number and size of nasal polyps over the course of the study as well as limited to no improvement in QOL.

LEVO patients are expected to exhibit mild to moderate improvement in the number and size of nasal polyps and/or mild to moderate improvement in QOL over the course of the study.

MONT patients are expected to exhibit mild to moderate improvement in the number and size of nasal polyps and/or mild to moderate improvement in QOL over the course of the study.

COMBO patients are expected to show a significant improvement in QOL, as compared to CONTROL, LEVO and MONT. COMBO patients are further expected to exhibit a significant decrease in the number and size of nasal polyps.

What is claimed is:

1. A method of treating a patient who has been exposed to radiation comprising administering to the patient an effective amount of a combination of levocetirizine and montelukast wherein the radiation exposure is associated with radiation therapy and wherein the combination ameliorates an inflammatory response associated with the radiation.

2. The method of claim 1, wherein the combination is administered at a time during radiation exposure.

3. The method of claim 1, wherein the combination is administered at a time after radiation exposure.

4. The method of claim 1, wherein the combination is administered in a sequential manner.

5. The method of claim 1, wherein the combination is administered in a substantially simultaneous manner.

6. The method of claim 1, further comprising the administration of a steroid.

7. The method of claim 1, wherein the combination is administered to the patient by one or more of the routes consisting of enteral, intravenous, intraperitoneal, inhalation, intramuscular, subcutaneous and oral.

8. The method of claim 7, wherein the levocetirizine and montelukast are administered by the same route.

* * * * *